(12) United States Patent
Yaku et al.

(10) Patent No.: US 7,585,400 B2
(45) Date of Patent: Sep. 8, 2009

(54) CHIP FOR ELECTROCHEMICAL IMMUNOASSAY

(75) Inventors: Hidenobu Yaku, Osaka (JP); Hirokazu Sugihara, Kanagawa (JP)

(73) Assignee: Panasonic Corporation, Osaka (JP)

( * ) Notice: Subject to any disclaimer, the term of this patent is extended or adjusted under 35 U.S.C. 154(b) by 142 days.

(21) Appl. No.: 11/976,950

(22) Filed: Oct. 30, 2007

(65) Prior Publication Data
US 2008/0308419 A1    Dec. 18, 2008

Related U.S. Application Data

(63) Continuation of application No. PCT/JP2007/060447, filed on May 22, 2007.

(30) Foreign Application Priority Data
Jul. 13, 2006    (JP)    ............... 2006-192581

(51) Int. Cl.
G01N 27/327    (2006.01)
(52) U.S. Cl. ............. 204/403.14; 435/7.9; 435/26; 204/403.01
(58) Field of Classification Search ........... 204/403.01, 204/403.14; 205/777.5, 792; 435/7.9, 26
See application file for complete search history.

(56) References Cited

FOREIGN PATENT DOCUMENTS

| | | |
|---|---|---|
| EP | 0 745 843 A2 | 12/1996 |
| JP | 55-13860 | 1/1980 |
| JP | 59-166084 | 9/1984 |
| JP | 2-62952 | 3/1990 |
| JP | 2-96649 | 4/1990 |
| JP | 7-110313 | 4/1995 |
| JP | 8-327852 | 12/1996 |
| JP | 9-297121 | 11/1997 |
| JP | 2004-24254 | 1/2004 |
| JP | 2005-46001 | 2/2005 |
| WO | WO 2005/108968 A1 | 11/2005 |

OTHER PUBLICATIONS

Maines et al, Analytica Chimica Acta 408 (2000), pp. 217-224.*
Katrlik et al, Analytica Chimica Acta 379 (1999), pp. 193-200.*
English translation of International Preliminary Report on Patentability and Written Opinion of the International Searching Authority issued for International Patent Application No. PCT/JP2007/060447, mailed Jan. 29, 2009.

* cited by examiner

Primary Examiner—Kaj K Olsen
(74) Attorney, Agent, or Firm—McDermott Will & Emery LLP

(57) ABSTRACT

The present invention provides a chip 100 that enables an immunoassay with high accuracy and without requiring a high volatile reagent. The chip 100 includes a chip substrate 20, a reagent mixture 12 and potassium ferricyanide 11 that are immobilized leaving a space in between on the chip substrate 20. The reagent mixture 12 includes at least one selected from NADP and NADPH, malate dehydrogenase, and a substrate of malate dehydrogenase. The chip 100 further includes diaphorase, immobilized on the chip substrate 20, as a part of or a component other than the reagent mixture 12.

3 Claims, 11 Drawing Sheets

CHIP FOR ELECTROCHEMICAL IMMUNOASSAY

RELATED APPLICATIONS

This application is a continuation of U.S. National Phase under 35 U.S.C. § 371 of International Application No. PCT/JP2007/060447, filed on May 22, 2007, which in turn claims the benefit of Japanese Application No. 2006-192581, filed on Jul. 13, 2006, the disclosures of which Applications are incorporated by reference herein.

TECHNICAL FIELD

The present invention relates to a chip for measuring the amount of target substances electrochemically using an immunoassay.

BACKGROUND ART

An immunoassay is a method of measuring the amount of target substances making use of the affinity between an antigen and an antibody, namely an antigen-antibody reaction. The antigen-antibody reaction exhibits the highest discriminability of target substances and has the most variety among biological phenomena known conventionally. For this reason, much attention is drawn to the immunoassay that enables direct measurement of target substances from a biological sample including a large variety of biomolecules without isolating and purifying the target substances.

FIG. 1 is a flow diagram for explaining one example of immunoassays. First, a sample solution 5 containing target substances 4 is added into a chamber 1 to which antibodies 2 are fixed (A1). Since each antibody 2 has an antigen-binding site for the target substances 4, the addition causes antigen-antibody reactions between the target substances 4 and the antibodies 2. Next, the chamber 1 is washed using a solution such as a buffer solution (A2). Impurities 3 possibly contained in the sample solution are removed from the chamber 1. Second antibodies 7 are then added into the chamber 1 (A3). Each second antibody 7 has an antigen-biding site that is not identical to the site of each antibody 2. The addition of the second antibodies 2 causes antigen-antibody reactions between the target substances 4 bound to the antibodies 2 and the second antibodies 7. Each second antibody 7 is labeled with a known labeling substance 6 such as a fluorescent substance, a radioactive substance and an enzyme. The chamber 1 is then washed again using a solution such as a buffer solution (A4) for removing second antibodies 7 that are not bound to the target substances 4 from the chamber 1. The amount of the target substances 4 is then calculated by measuring the amount of complexes, each composed of the antibody 2, the target substance 4 and the second antibody 7, remained in the chamber 1, more specifically, the amount of the labeling substances 6 labeling the second antibodies 7 of the complexes (A5).

FIG. 2 is a flow diagram for explaining another example of immunoassays. In this example, a solution containing labeled target substances 4b at a predetermined concentration is added with a sample solution containing target substances 4a into the chamber 1 (B1). The labeled target substances are mimic targets and each labeled target substance has an epitope identical to epitopes of the target substances 4a and is labeled with the labeling substance 6. The addition causes competitive antigen-antibody reactions are progressed in the chamber 1 between the antibodies 2 and the target substances 4a and between the antibodies 2 and the labeled target substances. The chamber 1 is then washed using a solution such as a buffer solution (B2) for removing substances such as impurities 3 possibly contained in the sample solution and unreacted labeled target substances from the chamber 1. The amount of the target substances 4a is then calculated by measuring the amount of the labeled target substances added into the chamber and the amount of complexes, composed of the antibody 2 and the labeled target substance, remained in the chamber 1, more specifically, the amount of the labeling substances 6 labeling the labeled target substances of the complexes (B3).

The immunoassay is not limited to the two examples mentioned above, and also can be performed by other assaying methods. The amount of the target substances in the sample solution is calculated on the basis of the amount of the labeling substances that reflects the amount of the target substances in any assaying method. Examples of the method of measuring the amount of the labeling substances include a method using a means of measuring the amount optically. Since this method requires a light source and a fluorescence detector, a device for the optical measurement is not easy to downsized and downscaled.

Much attention is drawn to a method employing an electrochemical means from the viewpoint of downsizing and downscaling a measurement device employed in the immunoassays as well as performing the assays in safety, easily and with high accuracy. JP 2(1990)-62952A and JP 9(1997)-297121A, for example, disclose a biosensor for measuring the amount of target substances in a sample making use of an enzymatic cycling reaction system that employs alkaline phosphatase as a labeling substance and potassium hexacyanoferrate(III) (potassium ferricyanide) as an electron mediator.

FIG. 3 is a diagram for explaining the enzymatic cycling reaction system employed in biosensors of JP 2(1990)-62952A and JP 9(1997)-297121A. This enzymatic cycling reaction system is composed of first to third reactions induced in a reaction solution containing alkaline phosphatase, oxidized nicotinamide adenine dinucleotide phosphate (NADP), ethanol, alcohol dehydrogenase, diaphorase, and potassium ferricyanide that is to be a substrate of diaphorase. In the first reaction, NADP is dephosphorylated by alkaline phosphatase and then converted into oxidized nicotinamide adenine dinucleotide (NAD). In the second reaction, a redox reaction through catalysis of alcohol dehydrogenase reduces the first reaction induced-NAD into reduced nicotinamide adenine dinucleotide (NADH) and oxidizes ethanol into acetaldehyde. In the third reaction, the second reaction-induced NADH is oxidized by potassium ferricyanide through catalysis of diaphorase and then converted into NAD, and the potassium ferricyanide is converted into potassium hexacyanoferrate(II) (potassium ferrocyanide). NADP may be replaced with reduced nicotinamide adenine dinucleotide phosphate (NADPH). Voltage application to the reaction solution converts the potassium ferrocyanide into potassium ferricyanide. Since the first to the third reactions are progressed in the reaction solution, the amount of the potassium ferrocyanide generated by the third reaction reflects the amount of the alkaline phosphatase contained in the reaction solution. The amount of the alkaline phosphatase is thus measured through a measurement of the amount of an oxidation current generated by the conversion from the potassium ferrocyanide into the potassium ferricyanide.

Long-term retainment of reagents involved in enzymatic cycling reactions in a chip is significant to provide a biosensor chip. The enzymatic cycling reaction system using alcohol dehydrogenase requires ethanol as mentioned above. Ethanol is not easily retained in the chip for a long time due to the high volatility. For this reason, a biosensor chip is not realized easily with the enzymatic cycling reaction system employing alcohol dehydrogenase.

DISCLOSURE OF INVENTION

The present inventor has established a novel enzymatic cycling reaction system not requiring a high volatile reagent. FIG. 4 is a diagram for explaining the novel enzymatic cycling reaction system. The primary reaction mechanism of this system is identical to that of the enzymatic cycling reaction system illustrated in FIG. 3. This novel enzymatic cycling reaction system employs malate dehydrogenase instead of the alcohol dehydrogenase, and at least one selected from malic acid and malate instead of ethanol. This novel enzymatic cycling reaction system is free from a high volatile reagent such as ethanol.

The novel enzymatic cycling reaction system illustrated in FIG. 4 is a reaction system independent of a lipid-modified enzyme. In order to suppress an oxidation current in a sample solution not containing a substrate (blank value), it was considered that enzymes and electron mediators, in a chip employing the enzymatic cycling reaction system independent of a lipid-modified enzyme, should be retained therein in a manner being strictly separated (for example, JP2005-46001A).

However, the present inventor found that retainment of enzymes and electron mediators being kept strictly separated in a chip enabled a blank value to be suppressed, but failed to improve a measuring accuracy of the chip to an extent of being enough practicable, as described in the Comparative Examples below.

The present inventor found that, in a chip, retainment of an electron mediator (potassium ferricyanide) being kept separated from enzymes and immobilization of another electron mediator (NADP or NADPH) at the same site as where the enzymes are immobilized enable a blank value to be suppressed and a measuring accuracy of the chip to be improved to an extent of being enough practicable, and the present invention was completed. The present invention provides a chip of measuring the amount of target substances electrochemically using an immunoassay. In the chip, at least one selected from NADP and NADPH, malate dehydrogenase, a substrate of malate dehydrogenase, potassium ferricyanide and diaphorase are immobilized. The malate dehydrogenase, the at least one selected from NADP and NADPH, and the substrate are mixed together. The malate dehydrogenase and the potassium ferricyanide are immobilized so as to leave a space in between.

According to the present invention, a chip that enables an immunoassay with high accuracy and without requiring a high volatile reagent can be provided.

DESCRIPTION OF THE PREFERRED EMBODIMENTS

Figure 4:
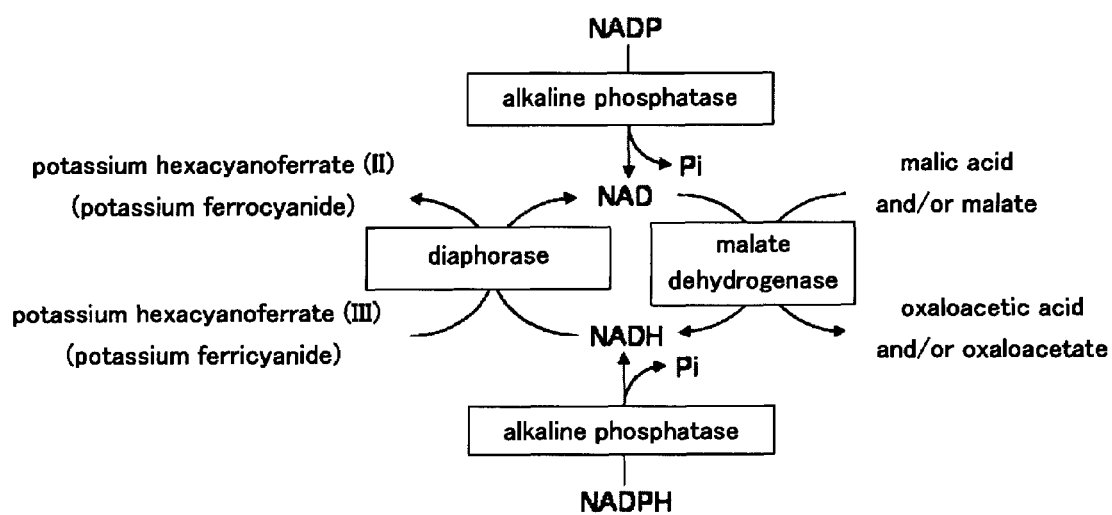
FIG. 4 is a diagram for explaining the novel enzymatic cycling reaction system.
Figure 5:
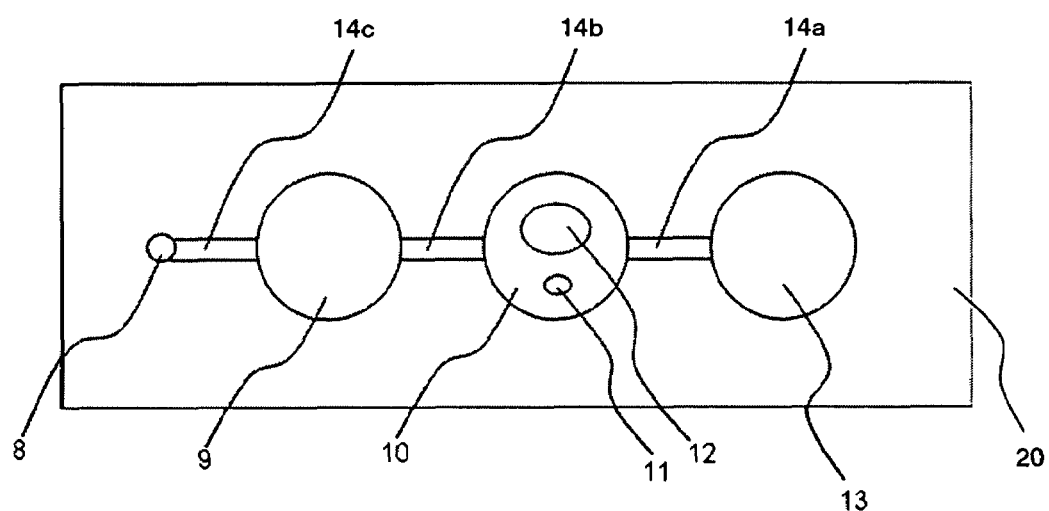
FIG. 5 is a diagram illustrating one example of the chips for performing the immunoassays.
Figure 6:
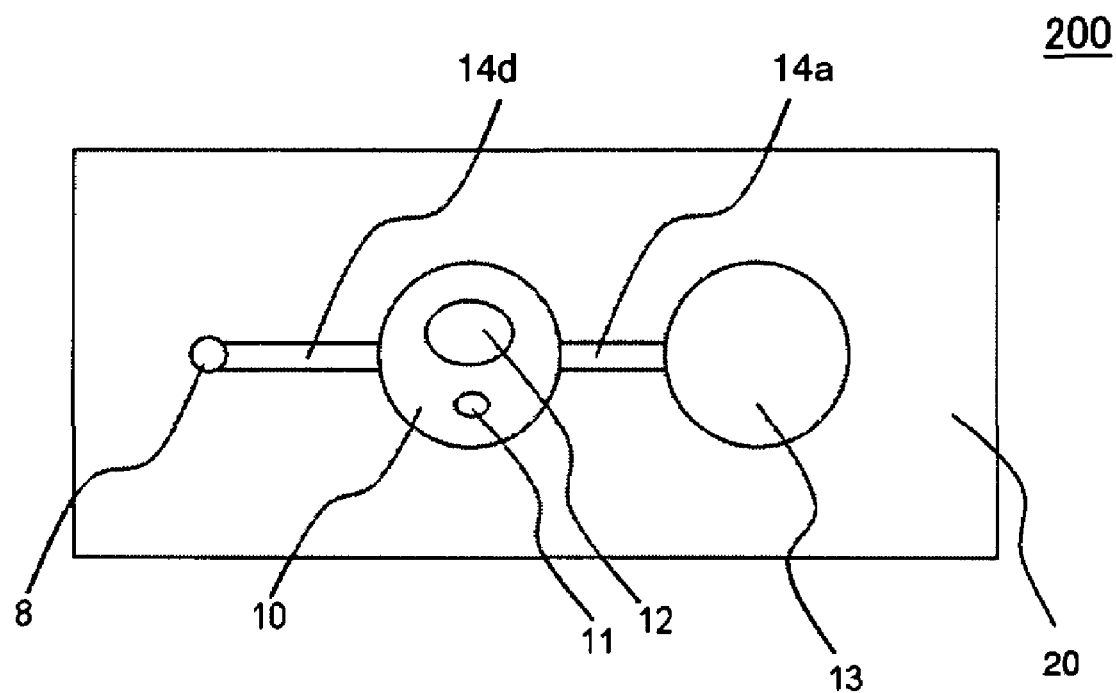
FIG. 6 is a diagram illustrating another example of the chips for performing the immunoassays.

FIGS. 5 and 6 are diagrams for explaining examples of chips for measuring the amount of target substances in a sample solution using the enzymatic cycling reaction system illustrated in FIG. 4.

As illustrated in FIG. 5, a chip 100 includes: an injection port 8 through which a sample solution is introduced into the chip; a reaction chamber 9 in which a solution containing alkaline phosphatase labeled substances, the amount of which reflects the amount of the target substances in the sample solution, is obtained; a reagent immobilized chamber 10; and an electrode chamber 13 in which electrodes for potentiometry are retained. The reagent immobilized chamber 10 and the electrode chamber 13 are connected to each other through a channel 14a. The reaction chamber 9 and the reagent immobilized chamber 10 are connected to each other through a channel 14b. The injection port 8 and the reaction chamber 9 are connected to each other through a channel 14c. As illustrated in FIG. 6, a chip 200 includes an injection port 8, a reagent immobilized chamber 10 and an electrode chamber 13. The reagent immobilized chamber 10 and the electrode chamber 13 are connected to each other through the channel 14a. The injection port 8 and the reaction chamber 9 are connected to each other through a channel 14d. The chambers and the channels are formed on a chip substrate 20. Examples of material for the chip substrate include polyethylene terephthalate (PET). The material for the chip substrate may be selected from glass and resins other than PET such as polycarbonate, polyimide and polypropylene.

Potassium ferricyanide 11 and a reagent mixture 12 are immobilized in the reagent immobilized chamber 10 in a manner of being desiccated and leaving a space in between. The reagent mixture 12 includes malate dehydrogenase, at least one selected from NADP and NADPH, and a substrate of malate dehydrogenase. Diaphorase also is immobilized, in a desiccated state, in the reagent immobilized chamber 10. In this description, "a reagent is immobilized in a chip" means a condition in which a reagent is retained in the chip at a strength that allows the reagent to be kept at its immobilized position even after somewhat strong shocks are applied to the chip. The reagent in such condition is easily dissolved in a sample solution. Examples of the substrate of malate dehydrogenase include at least one selected from malic acid and malate. Examples of the malate include at least one selected from potassium malate and sodium malate. The chips 100 and 200 of the present invention include a chip substrate 20, and potassium ferricyanide 11 and a reagent mixture 12 immobilized on the chip substrate 20 in a manner of leaving a space in between. The chips 100 and 200 further include diaphorase, immobilized on the chip substrate 20, as a part of or a component other than the reagent mixture 12.

Figure 1:
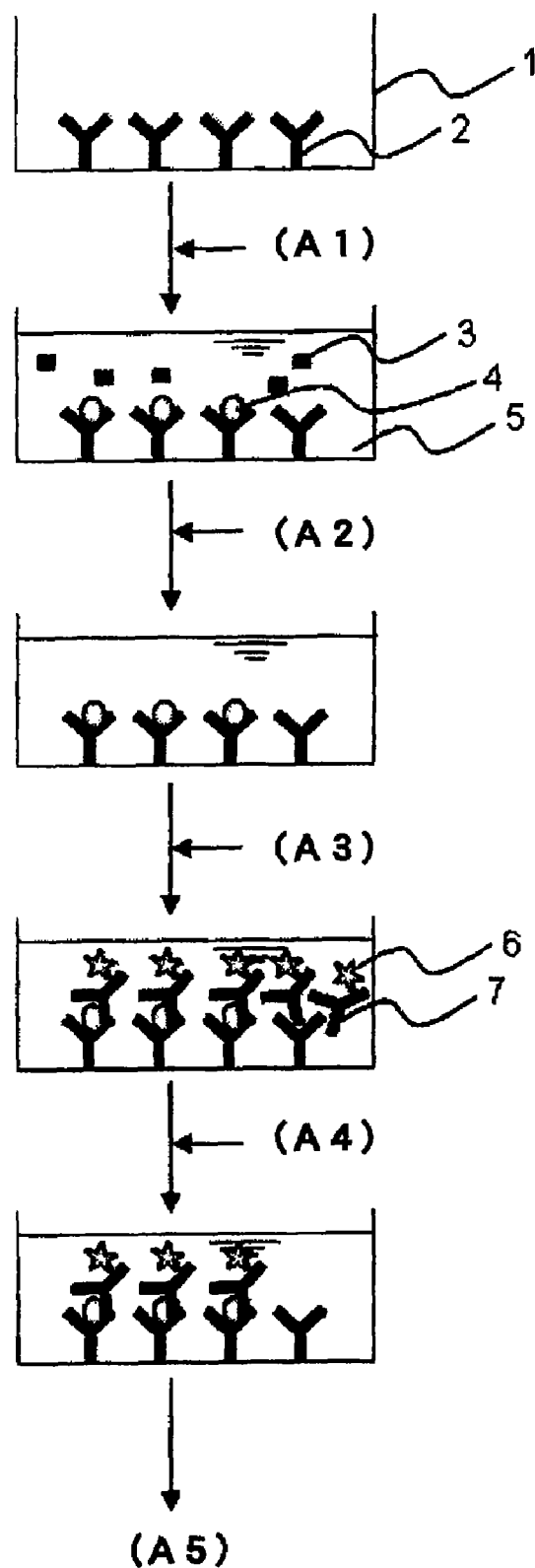
FIG. 1 is a flow diagram for explaining one example of immunoassays.
Figure 2:
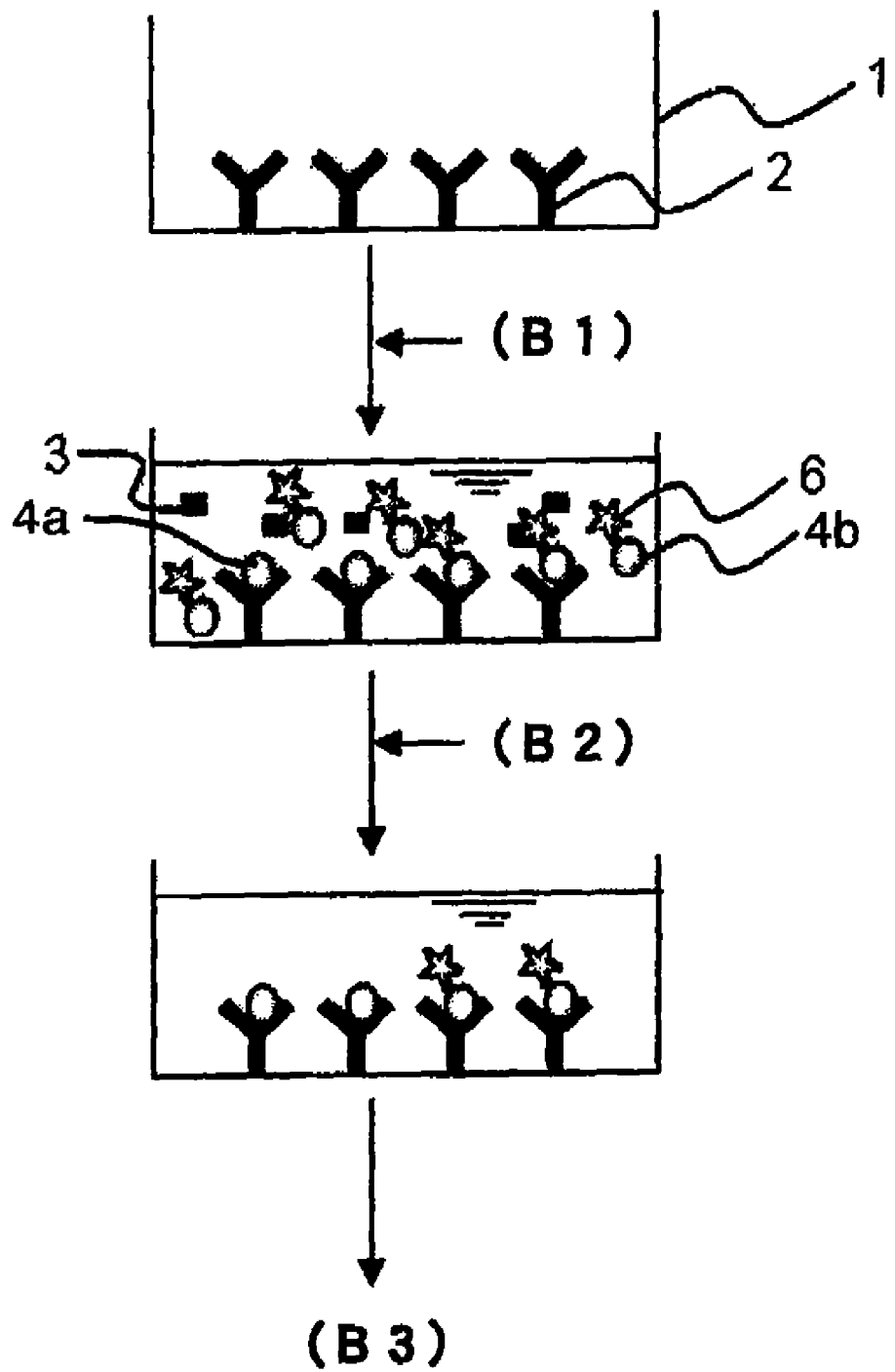
FIG. 2 is a flow diagram for explaining another example of immunoassays.
Figure 3:
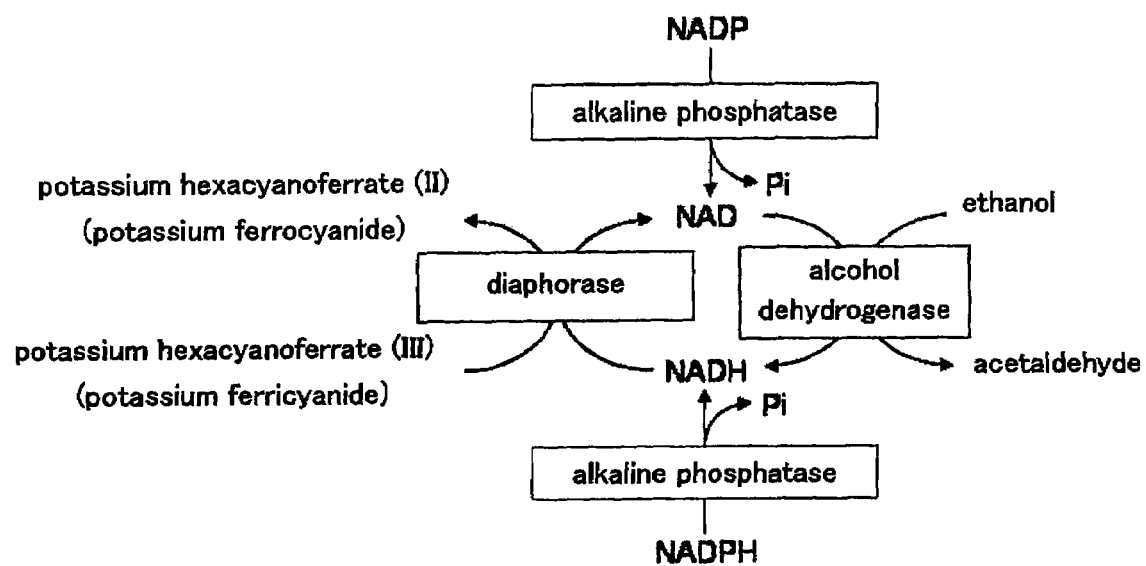
FIG. 3 is a diagram for explaining the enzymatic cycling reaction system using alcohol dehydrogenase.

In the chip 100, a sample solution introduced from the injection port 8 is sent to the reaction chamber 9 through the channel 14c. A solution containing alkaline phosphatase labeled substances, the amount of which reflects the amount of target substances in the sample solution, is prepared in the reaction chamber 9. This solution is then sent to the reagent immobilized chamber 10 through the channel 14b. Examples of reactions for obtaining this solution include various series of reactions illustrated in the flow diagrams of FIGS. 1 and 2. The number and arrangement of chambers and channels composing the reaction chamber 9 can be determined based on reactions to be caused in the reaction chamber 9.

In the chip 200, a solution containing alkaline phosphatase labeled substances, the amount of which reflects the amount of target substances in a sample solution, is introduced to the reagent immobilized chamber 10 from the injection port 8 through the channel 14d. The solution containing the alkaline phosphatase labeled substances is prepared by a chip user before the introduction.

In the chips 100 and 200, introduction of the solution containing alkaline phosphatase labeled substances to the reagent immobilized chamber 10 causes dissolution of the reagents mentioned above, from potassium ferricyanide to diaphorase, in the solution. In the reagent immobilized chamber 10, the cycling reaction illustrated in FIG. 4 is then progressed among the alkaline phosphatase in the solution and the reagents. The solution is sent to the electrode chamber 13 through the channel 14a. In the electrode chamber 13, voltage application to the solution is performed to convert potassium ferrocyanide obtained through the cycling reaction to potassium ferricyanide. The amount of current generated by the conversion is measured (potentiometry). The amount of the target substances in the sample solution is calculated by measuring the amount of the current obtained through the potentiometry.

The reagents concerned with the enzymatic cyclic reaction illustrated in FIG. 4 may be immobilized in the channels 14a, 14b, 14d and the electrode chamber 13 instead of the reagent immobilized chamber 10 at a state of being able to be dissolved in a sample solution. The electrode chamber 13 may have an electrode system such as a bipolar system composed of a working electrode and a counter electrode; and a tripolar system composed of a working electrode, a counter electrode and a reference electrode. The solution may be sent from one to another among the chambers, for example, using a centrifugal force or a pressure applied to the channels with a pump.

Hereinafter, the present invention is described further in detail using examples.

Figure 7:
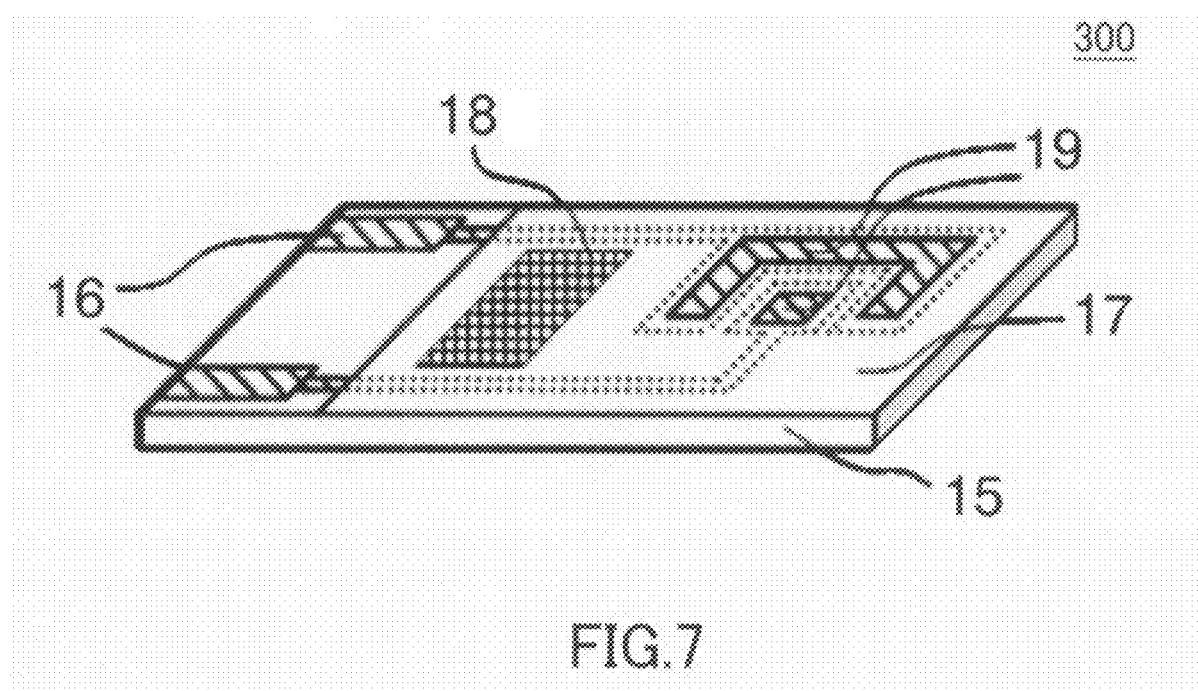
FIG. 7 is a diagram illustrating the chip used in Example and Comparative Examples.

A chip 300 illustrated in FIG. 7 was prepared. The chip 300 included: a chip substrate 15 made of PET; an electrode system 16 composed of a counter electrode and a measuring electrode disposed on the chip substrate 15; and an insulating layer 17 disposed on the chip substrate 15. The electrode system 16 may be formed through screen-printing a known conductive carbon paste onto the chip substrate 15 in a predetermined arrangement, followed by heating and drying the paste. The insulating layer 17 may be formed through screen-printing a known insulating paste followed by heating and drying the insulating paste. This insulating layer 17 should be formed such that an electrode exposed position 19 where a portion of the electrode system 16 is exposed and another portion of the electrode system 16 also is exposed to apply a voltage to the electrode system 16. A part of the surface of the insulating layer 17 was used as a reagent immobilized position 18 where the reagents, in a desiccated state, concerned with the enzymatic cycling reaction illustrated in FIG. 4 were immobilized.

COMPARATIVE EXAMPLE 1

A mixed solution was prepared by mixing the following solutions: a 1M potassium ferricyanide solution (1 μL); a 1000 U/mL diaphorase solution (6.7 μL); a 4M sodium malate solution (7.8 μL); a 5 mM NADP solution (1 μL); a 25000 U/mL malate dehydrogenase solution (1 μL); and a 1M Tris-HCl solution (5 μL, pH 9). The mixed solution (22.5 μL) was placed on the reagent immobilized position 18 and then vacuum dried at room temperature (25° C.) for three hours to desiccate and immobilize all the reagents concerned with the enzymatic cycling reaction illustrated in FIG. 4 on the reagent immobilized position 18 in a mixed state.

Next, reaction solutions were prepared. Each solution was prepared by adding a solution containing alkaline phosphatase labeled CRP antibodies (100 μL) to the reagents on the reagent immobilized position 18, and dissolving the reagents into the solution. The concentrations of the alkaline phosphatase labeled CRP antibodies in the reaction solutions were 0 M, 0.083 nM, 0.415 nM, and 0.830 nM.

Reaction solutions were incubated at 30° C. for ten minutes and then moved onto the electrode exposed position 19 of the chip 300. A constant voltage of 400 mV was applied to each reaction solution for performing the potentiometry.

Figure 8:
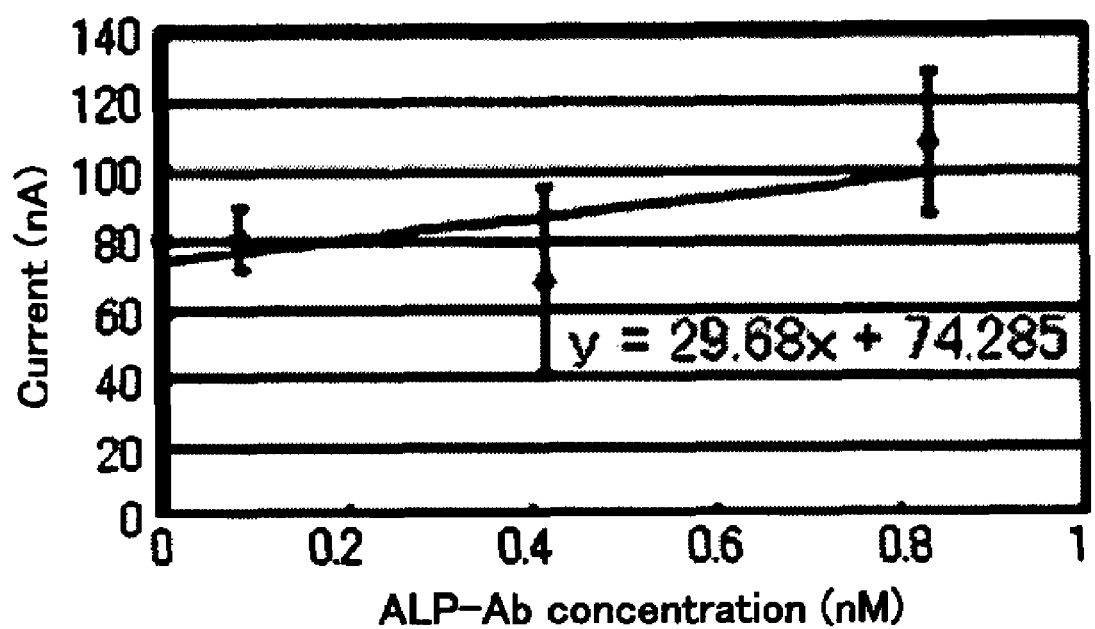
FIG. 8 is a graph illustrating the result of potentiometry obtained in Comparative Example 1.

FIG. 8 is a graph illustrating the relationship between the concentration of the alkaline phosphatase labeled CRP antibodies (ALP-Ab concentration) in the reaction solution and the amount of current flowed in each reaction solution directly after the voltage application, in Comparative Example 1. As illustrated in FIG. 8, the amounts of current obtained through the potentiometry were scattered widely, and each amount was less correlated with the ALP-Ab concentration. Thus, it is difficult to measure the amount of the target substances with high accuracy using the chip of Comparative Example 1.

COMPARATIVE EXAMPLE 2

The potentiometry was performed in the same manner as in Comparative Example 1 except that the reagents concerned with the enzymatic cycling reaction illustrated in FIG. 4 were desiccated and immobilized on a reagent immobilized position 18 of the chip 300 to keep the electron mediators (potassium ferricyanide and NADP) and enzymes (malate dehydrogenase and diaphorase) separated from each other.

The reagents were desiccated and immobilized as follows. A mixed solution was prepared by mixing a 1000 U/mL diaphorase solution (6.7 μL), a 4M sodium malate solution (7.8 μL), a 25000 U/mL malate dehydrogenase solution (1 μL) and a 1M Tris-HCl solution (5 μL, pH 9). A 1M potassium ferricyanide solution (1 μL) and a 5 mM NADP solution (1 μL) were prepared. The mixed solution (20.5 μL), the potassium ferricyanide solution (1 μL) and the NADP solution (1 μL) were placed on separate sites of the reagent immobilized position 18 and then vacuum dried at room temperature for three hours.

Figure 9:
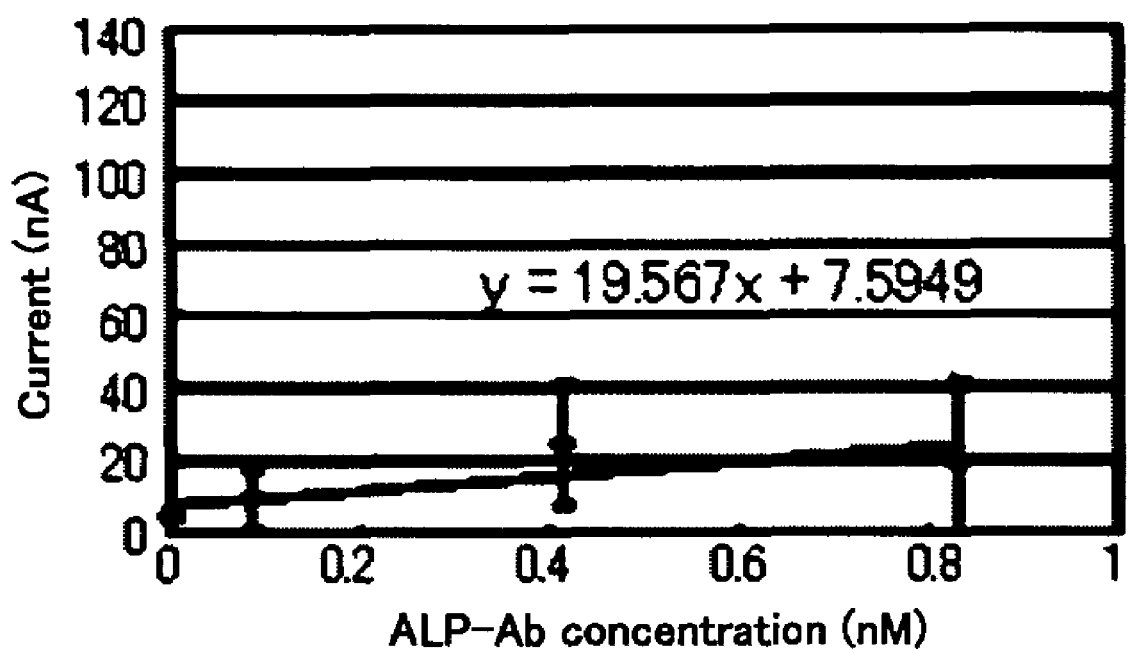
FIG. 9 is a graph illustrating the result of potentiometry obtained in Comparative Example 2.

FIG. 9 is a graph illustrating the relationship between the ALP-Ab concentration in the reaction solution and the amount of current flowed in each reaction solution directly after the voltage application, in Comparative Example 2. As illustrated in FIG. 9, a blank value included in the amount of current, obtained through the potentiometry, was smaller than the value in Comparative Example 1, but the amounts of current obtained here were still highly dispersed. Furthermore, the slope of the fitted line (slope of the calibration curve) on the plots of the amount of current was smaller than that of Comparative Example 1. Thus, it is difficult to measure the amount of the target substances with high accuracy using the chip of Comparative Example 2.

Example 1

The potentiometry was performed in the same manner as in Comparative Example 2 except that the reagents concerned with the enzymatic cycling reaction illustrated in FIG. 4 desiccated and immobilized on a reagent immobilized position 18 of the chip 300 to keep potassium ferricyanide of the electron mediators separated from the enzymes and their substrates.

The reagents were desiccated and immobilized as follows. A mixed solution was prepared by mixing a 1000 U/mL diaphorase solution (6.7 µL), a 4M sodium malate solution (7.8 µL), a 5 mM NADP solution (1 µL), a 25000 U/mL malate dehydrogenase solution (1 µL) and a 1M Tris-HCl solution (5 µL, pH 9). A 1M potassium ferricyanide solution (1 µL) was prepared. The mixed solution (21.5 µL) and the potassium ferricyanide solution (1 µL) were placed on separate sites of the reagent immobilized position 18 and then vacuum dried at room temperature for three hours.

Figure 10:
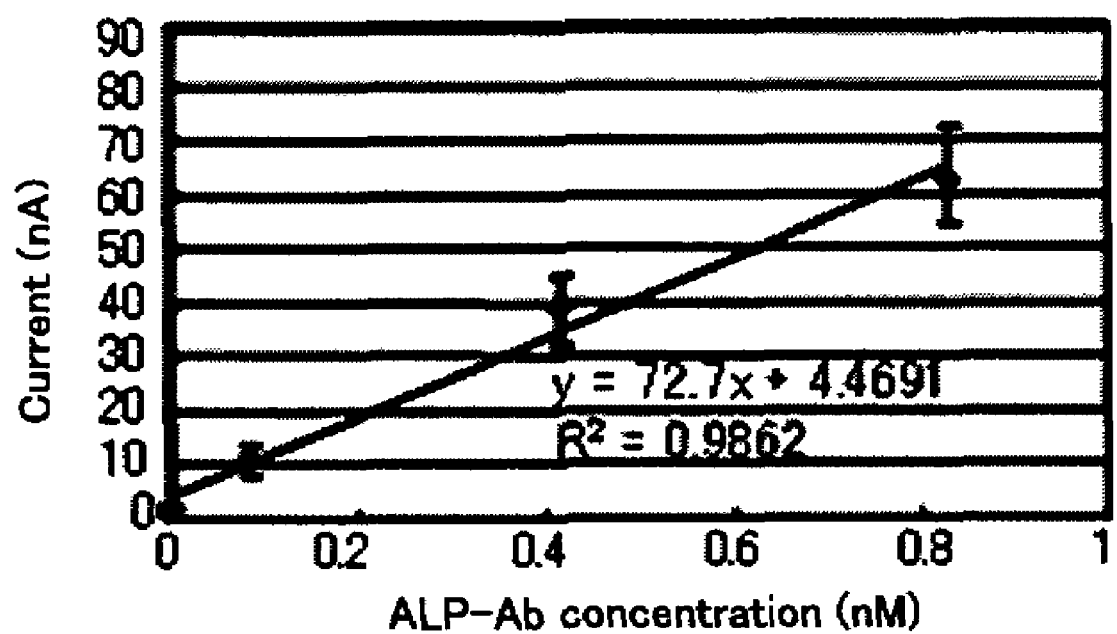
FIG. 10 is a graph illustrating the result of potentiometry obtained in Example 1.

FIG. 10 is a graph illustrating the relationship between the ALP-Ab concentration in the reaction solution and the amount of current flowed in each reaction solution directly after the voltage application, in Example 1. As illustrated in FIG. 10, the amount of current obtained through the potentiometry was highly correlated with the ALP-Ab concentration. Thus, the amount of the target substances can be measured with high accuracy using the chip of Example 1.

COMPARATIVE EXAMPLE 3

The potentiometry was performed in the same manner as in Comparative Example 2 except that the reagents concerned with the enzymatic cycling reaction illustrated in FIG. 4 desiccated and immobilized on a reagent immobilized position 18 of the chip 300 to keep NADP of the electron mediators separated from the enzymes and their substrates.

The reagents were desiccated and immobilized as follows. A mixed solution was prepared by mixing a 1M potassium ferricyanide solution (1 µL), a 1000 U/mL diaphorase solution (6.7 µL), a 4M sodium malate solution (7.8 µL), a 25000 U/mL malate dehydrogenase solution (1 µL) and a 1M Tris-HCl solution (5 µL, pH 9). A 5 mM NADP solution (1 µL) were prepared. The mixed solution (21.5 µL) and the NADP solution (1 µL) were placed on separate sites of the reagent immobilized position 18 and then vacuum dried at room temperature for three hours.

Figure 11:
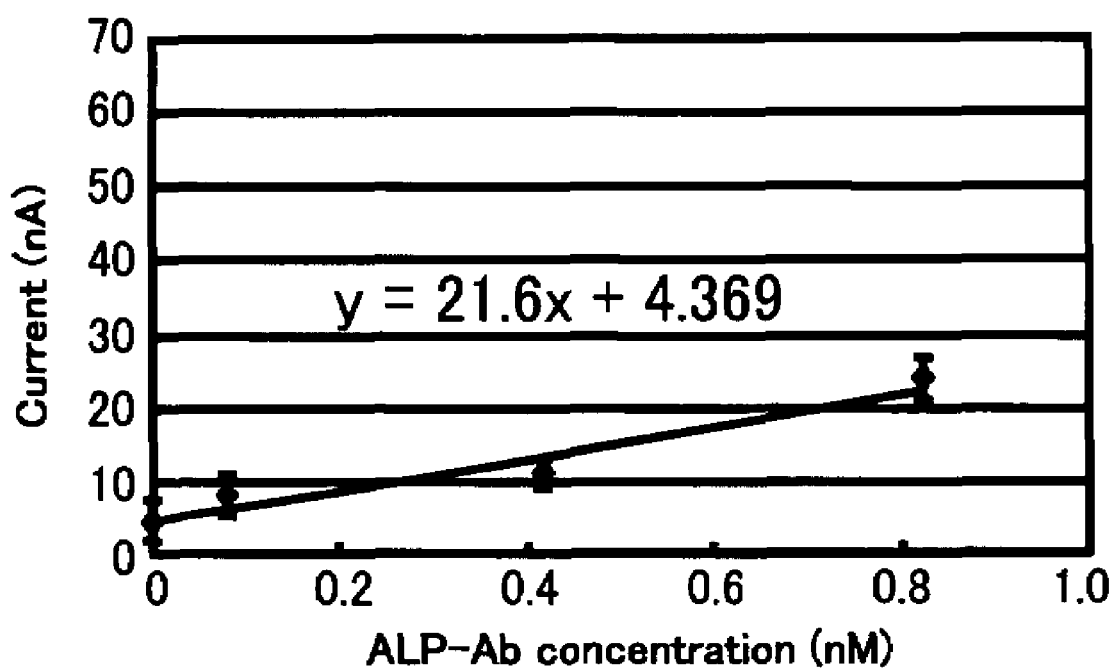
FIG. 11 is a graph illustrating the result of potentiometry obtained in Comparative Example 3.

FIG. 11 is a graph illustrating the relationship between the ALP-Ab concentration in the reaction solution and the amount of current flowed in each reaction solution directly after the voltage application, in Comparative Example 3. As illustrated in FIG. 11, the slope (21.6) of the fitted line on the plots of the amount of current, obtained through the potentiometry, was small, less than a third of the slope (72.7) obtained in Example 1. Thus, it is difficult to measure the amount of the target substances, using the chip of Comparative Example 3, with high accuracy comparable to the chip of Example 1.

INDUSTRIAL APPLICABILITY

The present invention provides a chip that enables an immunoassay with high accuracy and without requiring a high volatile reagent.

What is claimed is:
1. A chip for measuring an amount of target substances electrochemically using an immunoassay, the chip comprising:
    electrodes composed of a working electrode and a counter electrode, or of a working electrode, a counter electrode and a reference electrode,
    wherein, in the chip, at least one selected from NADP and NADPH, malate dehydrogenase, a substrate of malate dehydrogenase, potassium ferricyanide and diaphorase are immobilized, and
    wherein the malate dehydrogenase, the at least one selected from NADP and NADPH, and the substrate are mixed and immobilized together, and
    wherein the malate dehydrogenase and the potassium ferricyanide are immbolized so as to leave a space in between.
2. The chip according to claim 1, wherein the substrate of the malate dehydrogenase includes at least one selected from malic acid and malate.
3. The chip according to claim 1, wherein the malate includes at least one selected from potassium malate and sodium malate.

* * * * *

UNITED STATES PATENT AND TRADEMARK OFFICE
CERTIFICATE OF CORRECTION

| | |
|---|---|
| PATENT NO. | : 7,585,400 B2 |
| APPLICATION NO. | : 11/976950 |
| DATED | : September 8, 2009 |
| INVENTOR(S) | : Hidenobu Yaku et al. |

Page 1 of 1

It is certified that error appears in the above-identified patent and that said Letters Patent is hereby corrected as shown below:

In Column 8, Line 39 (Claim 1), change "immbolized" to --immobolized--.

Signed and Sealed this

Sixteenth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,585,400 B2
APPLICATION NO. : 11/976950
DATED : September 8, 2009
INVENTOR(S) : Hidenobu Yaku et al.

Page 1 of 1

It is certified that error appears in the above-identified patent and that said Letters Patent is hereby corrected as shown below:

In Column 8, Line 39 (Claim 1), change "immbolized" to --immobilized--.

This certificate supersedes the Certificate of Correction issued on March 16, 2010.

Signed and Sealed this
Twenty-second Day of February, 2011

David J. Kappos
*Director of the United States Patent and Trademark Office*